(12) United States Patent
Matthews

(10) Patent No.: US 11,179,259 B2
(45) Date of Patent: Nov. 23, 2021

(54) ORTHOTIC SHOULDER SUPPORT

(71) Applicant: DM Orthotics Limited, Redruth (GB)

(72) Inventor: Martin Matthews, Redruth (GB)

(73) Assignee: DM ORTHOTICS LIMITED

( * ) Notice: Subject to any disclaimer, the term of this patent is extended or adjusted under 35 U.S.C. 154(b) by 484 days.

(21) Appl. No.: 15/981,106

(22) Filed: May 16, 2018

(65) Prior Publication Data
US 2019/0274858 A1   Sep. 12, 2019

(30) Foreign Application Priority Data

Mar. 6, 2018  (GB) .................................. 1803593.1

(51) Int. Cl.
*A61F 5/01*       (2006.01)
*A63B 21/00*      (2006.01)
(Continued)

(52) U.S. Cl.
CPC ........ *A61F 5/0118* (2013.01); *A63B 21/4005* (2015.10); *A63B 21/4017* (2015.10);
(Continued)

(58) Field of Classification Search
CPC ............ A61F 5/0118; A61F 2005/0151; A61F 2005/0153; A61F 2005/0179;
(Continued)

(56) References Cited

U.S. PATENT DOCUMENTS

D571,016  S      6/2008  Matthews
2003/0208146 A1 11/2003  Kania
(Continued)

FOREIGN PATENT DOCUMENTS

EP  0226068   12/1988
EP  3034052    8/2017

OTHER PUBLICATIONS

Matthews et al., "The Use of a Dynamic Elastomeric Fabric Orthosis to Manage Painful Shoulder Subluxation: A Case Study American Academy of Orthotists and Prosthetists", vol. 23, No. 3, 2011.

(Continued)

*Primary Examiner* — Camtu T Nguyen
(74) *Attorney, Agent, or Firm* — Gardner Groff & Greenwald, PC

(57) ABSTRACT

An orthotic support comprises a shoulder section for encapsulating a first shoulder of a wearer, a glove section for conforming to at least a portion of the wearer's hand, and a sleeve section for conforming to the wearer's arm, the sleeve section connecting the shoulder section to the glove section. A resilient reinforcement extends from the glove section to the shoulder section, and at least a portion of the reinforcement extends in a spiral around the sleeve section, so that the reinforcement is configured to apply a rotational force to the wearer's arm, when worn, to urge a portion of the wearer's arm to rotate in a predetermined direction. The orthotic support may be usable to treat or prevent shoulder dislocation or subluxation, arm over-pronation or over-supination, wrist flexion or elbow flexion. An orthotic support may comprise a reinforcement with a first branch extending over an anterior portion of the sleeve section, and a second branch extending over a posterior portion of the sleeve section, so that the reinforcement is configured to urge the wearer's upper arm towards a rest position.

22 Claims, 7 Drawing Sheets

(51) Int. Cl.
*A63B 23/12* (2006.01)
*A61F 13/14* (2006.01)
*A61H 1/02* (2006.01)
*A63B 21/02* (2006.01)
*A63B 21/055* (2006.01)

(52) U.S. Cl.
CPC ...... *A63B 21/4025* (2015.10); *A63B 23/1245* (2013.01); *A63B 23/1281* (2013.01); *A61F 13/146* (2013.01); *A61F 2005/0151* (2013.01); *A61F 2005/0153* (2013.01); *A61F 2005/0179* (2013.01); *A61F 2005/0181* (2013.01); *A61H 1/0277* (2013.01); *A61H 1/0281* (2013.01); *A61H 1/0285* (2013.01); *A61H 2201/165* (2013.01); *A63B 21/02* (2013.01); *A63B 21/0552* (2013.01)

(58) Field of Classification Search
CPC ............ A61F 2005/0181; A61F 13/146; A61F 5/024; A61F 5/026; A61F 5/028; A61F 2005/0197; A61F 5/37; A63B 21/4005; A63B 21/4017; A63B 21/4025; A63B 21/1425; A63B 23/1281; A63B 21/02; A63B 21/0552; A63B 23/1245; A61H 1/0281; A61H 1/0285; A61H 2001/165; A61H 1/0277; A61H 2201/165; A41D 1/007; A41D 13/08; A41D 13/0015; A41D 27/10; A41D 31/18; A41D 31/185; A41D 2600/10
See application file for complete search history.

(56) References Cited

U.S. PATENT DOCUMENTS

| | | |
|---|---|---|
| 2004/0193086 A1* | 9/2004 | Cofre .................... A61F 5/3738 602/20 |
| 2014/0024987 A1 | 1/2014 | Anglada |
| 2015/0374529 A1 | 12/2015 | Summit |
| 2016/0213504 A1* | 7/2016 | Colleran .................. A41B 1/08 |
| 2017/0246071 A1* | 8/2017 | Schultz ................ A61G 5/1043 |
| 2018/0036161 A1 | 2/2018 | Alvarez |

OTHER PUBLICATIONS https://www.dmorthotics.com/product/dmo-glove, accessed Sep. 5, 2018.
https://www.dmorthotics.com/product/dmo-single-shoulder-orthosis, accessed Sep. 5, 2018.
International Search Report and Written Opinion of the International Bureau of the World Intellectual Property Organization, dated May 31, 2019.
Yasukawa, Audrey, Martin, Patricia, Guilford, Arthur,, Mukherjee, Shubhra, "Case Study: Use of the Dynamic Movement Orthosis to Provide Compressive Shoulder Support for Children with Brachial Plexus Palsy," JPO Journal of Prosthetics and Orthotics, 2011, vol. 23, No. 3, pp. 159-164, American Academy of Orthotists and Prosthetists, Bethesda. Maryland.

* cited by examiner

ORTHOTIC SHOULDER SUPPORT

CROSS-REFERENCE TO RELATED APPLICATION

This application claims priority to GB Patent Application Serial No. 1803593.1 filed Mar. 6, 2018, which is hereby incorporated herein by reference.

TECHNICAL FIELD

This invention relates to an orthotic support, or orthosis, in particular an orthotic shoulder support. Particularly preferably the invention relates to an orthotic support for a wearer's hand, elbow and shoulder.

BACKGROUND

Common shoulder injuries include dislocation or subluxation. The risk of shoulder injury is increased for individuals whose shoulder joints are maintained in a less than optimal orientation.

For example, individuals may have a shoulder instability in one shoulder, which may lead to an inability to maintain the humeral head in the glenoid fossa during active motion. An individual may have a shoulder instability in both shoulders. Shoulder instability may result from a sub-optimal positioning of the scapula or scapula instability. A sub-optimal positioning of the scapula may result from a pre-existing condition or injury, or from body positioning during performance of an activity such as a sport.

Strapping and/or taping an individual's shoulders may help to maintain an optimal shoulder position. However, this process can be time consuming and can require another person to apply the strapping and tape correctly. In most cases, the strapping and taping must be undertaken by a physiotherapist or some other person with the required level of skill and knowledge.

A number of medical conditions may also result in shoulder instability, subluxation, and poor muscular control of the shoulder joint. Road traffic trauma, sport injury, the after-effects of a stroke, and conditions such as cerebral palsy and other neuro-muscular conditions, for example, may result in shoulder instability.

The same medical conditions may also result in abnormal muscular tone and poor control of an individual's upper limbs. For example, individuals that have suffered a stroke, or who suffer from cerebral palsy or multiple sclerosis, may experience problems such as over-pronation of forearms, or difficulty with flexion or extension of wrist joints.

SUMMARY OF INVENTION

The invention provides an orthotic support as defined in the appended independent claims to which reference should now be made. Advantageous or preferred features are set forth in dependent claims.

According to a first aspect, the invention may provide an orthotic support comprising: a shoulder section for encapsulating a first shoulder of a wearer, configured to be anchored to the wearer's torso;
a glove section for conforming to at least a portion of the wearer's hand;
a sleeve section for conforming to the wearer's arm, the sleeve section connecting the shoulder section to the glove section,
each of the shoulder section, the glove section and the sleeve section comprising an elastomeric base material; and
a resilient reinforcement, connected to the base material, which extends from the glove section to the shoulder section,
wherein at least a portion of the reinforcement extends in a spiral around the sleeve section, so that the reinforcement is configured to apply a rotational force to the wearer's arm, when worn, to urge a portion of the wearer's arm to rotate in a predetermined direction.

The orthotic support of the present invention may be termed an orthotic shoulder support, a shoulder and arm orthosis, or a combined shoulder and arm orthosis. Preferably the orthotic support may be termed a hand-elbow-shoulder orthosis.

The sleeve section is configured to receive at least a portion of a user's arm, and may be described as a sleeve.

The sleeve section is advantageously permanently connected, or attached, to the glove section at a first, lower, end of the sleeve section, and permanently connected, or attached, to the shoulder section of the orthosis at a second, upper, end of the sleeve section.

The glove section and the sleeve section may advantageously be configured to receive and conform to a wearer's hand and arm. In particular, the glove and sleeve sections may be configured to receive and conform to the wearer's hand, wrist, forearm, elbow and upper arm. The shoulder section is configured to receive and conform to the wearer's shoulder. When the orthotic support is worn, the wearer's shoulder, arm and hand are received in the orthotic support.

By providing a glove section and a sleeve section connected to the shoulder section, the orthotic support may advantageously ensure that both the wearer's shoulder and arm are supported in a desired position when the orthotic support is worn. The orthotic device may thus simultaneously address problems with both the wearer's shoulder and their arm.

Particularly advantageously, providing an orthotic support in which a sleeve and glove section are connected to the shoulder section may ensure that the sleeve and glove are always correctly aligned when the orthotic support is donned by the wearer.

In order to have the intended correctional effect on a body part, it is important that orthoses are worn correctly.

Orthotic gloves known in the prior art may comprise a sleeve which extends up a portion of a user's arm to address muscular conditions relating to the arm. However, a shortcoming of such gloves is that the sleeve may be incorrectly aligned when worn, which may reduce, or undesirably increase, the correctional effect of the glove on the user's arm. For example, the upper end of the sleeve may be twisted relative to its intended position on the user's arm, which may alter its intended effect on the arm. This may significantly lessen the effectiveness of the orthosis, and may slow the user's rehabilitation.

In the present invention, the sleeve and glove portion are permanently connected to the shoulder section of the orthosis. This may advantageously ensure that the sleeve is always correctly aligned when the support is worn, as the upper end of the sleeve is fixed in position relative to the wearer's shoulder, and the lower end of the sleeve is fixed in position relative to the wearer's hand. As the shoulder section is configured to encapsulate the wearer's shoulder, the shoulder section of the orthotic support is automatically positioned on the shoulder when the device is donned. The sleeve is connected to the shoulder section, so the sleeve cannot be rotated around the wearer's arm out of its intended alignment. This may advantageously ensure that the reinforcement is always retained in its intended alignment with the wearer's body, so that the first force is repeatably and consistently applied to the wearer's body.

The orthotic support may comprise one or more elastomeric base materials. The shoulder section, the glove section and the sleeve section may comprise the same elastomeric base materials, or different elastomeric base materials. The support may comprise a plurality of panels of elastomeric base material, connected together to form a one-piece orthotic support, or orthosis. Panels of elastomeric base material may be connected, for example, by stitching or ultrasonic welding. Alternatively, one or more sections of the orthotic support may be formed by circular knitting.

The elastomeric base material preferably provides a base layer, or underlying layer, to which the resilient reinforcement may be attached. The elastomeric base material is preferably a resilient or elastomeric material that is capable of conforming to the wearer's body without generating substantial directional forces, or giving rise to lines of tension or compression in any specific direction. Suitable materials are readily available, for example elastomeric materials comprising a polyurethane-polyurea copolymer such as DORLASTAN, SPANDEX, or LYCRA.

The orthotic support may comprise an underlying support, formed from one or more elastomeric base materials, comprising a shoulder section, a sleeve section, and a glove section.

The orthotic support may comprise one or more resilient reinforcements. Different resilient reinforcements may advantageously be configured to apply different forces to the wearer's body when the orthotic support is worn.

Preferably, the resilient reinforcement comprises one or more strips or panels of resilient material or elastic material that are attached, or connected, to the elastomeric base material to provide a tension force or compression force to a portion of the wearer's body. The resilient reinforcement is preferably permanently attached to the elastomeric base material, for example by stitching. The resilient reinforcement is preferably connected to the elastomeric base material by stitching along all of the edges of the resilient reinforcement.

A resilient material is a material that can elastically deform under load and return to its original shape when the load is removed, for example rubber materials or elastomeric fabric materials.

In preferred embodiments, panels or strips of resilient reinforcement material may be attached to the elastomeric base material in a non-tensioned condition, i.e. the panels or strips do not have a force applied to them as they are attached to the underlying elastomeric base material forming the shoulder, sleeve and glove sections, and do not exert a force on the underlying elastomeric base material. In this configuration each reinforcement panel or strip may, when the orthotic support is worn, apply a resistive force acting in a specific direction when a portion of a wearer's body is moved in a direction that causes the panel or strip to stretch.

The force generated by an individual strip or panel of reinforcement material is preferably applied to the wearer's body in the direction of a longitudinal axis of the strip or panel. More than one strip or panel may be used in conjunction such that the sum of the forces applied by the strips or panels results in a net force that is applied to the wearer's body in a direction that is not coincident with a longitudinal axis of any one panel or strip.

Advantageously, panels or strips of resilient reinforcement material may be attached to the glove section, the sleeve section, and the shoulder section such that they become stretched automatically when the support is worn. Thus, the resilient reinforcement panels or strips may, once the support has been donned by a wearer, provide a continuous force urging a portion of the wearer's body in a predetermined direction.

In some embodiments, one or more strips or panels of resilient reinforcement material may be attached to the elastomeric base material in a pre-tensioned condition, i.e. the panels or strips are stretched and then attached to the underlying material while stretched. In this configuration the panels or strips are able to exert a force on a wearer's body that continually urges the wearer's body in the direction of the applied force. The force generated by a pre-tensioned strip or panel will resist movement of a wearer's body in a direction that causes the strip or panel to stretch further.

Preferably, the orthotic support still allows the full range of active shoulder and arm movement, even though forces may act to urge the wearer's shoulder and arm in a specific direction.

Properties of the reinforcement panels, such as panel width or panel thickness or panel material, may be varied to increase or decrease the magnitude of the applied force. The position or shape of the reinforcement panels may be varied in order to vary the direction of the applied force.

Reinforcement panels may be positioned over pre-existing seams in the underlying support, for example, seams joining panels that form the sleeve and the shoulder section. Alternatively, seams, such as seams joining panels to form the glove section or the shoulder section, may be formed over the top of reinforcement panels.

The positioning of various parts of the orthotic support, and in particular any resilient reinforcements, is important in order to determine the forces applied to the wearer's body by the support when it is worn. The arrangement and orientation of reinforcements, or other panels, on the orthotic support will be described herein with reference to the wearer's body when the device is worn, with reference to the wearer's body in the standard anatomical position, as shown in FIG. 1.

The orthotic support may enhance the wearer's proprioception i.e. the individual's subconscious awareness of their shoulder and arm position. Thus, the wearer may be made aware of when their shoulder and/or arm is in an optimal or sub-optimal position. For example, the resilient reinforcement may provide resistance which informs the wearer as to when the arm is being moved into an undesirable position. The wearer may thus be less likely to overexert the arm or the shoulder. The first force may also mechanically resist movement of the arm into an undesirable position.

The support may thus provide a pre-fabricated shoulder support, reducing the need for strapping and tape. The wearer may put on the support such that the reinforcements are automatically placed in the correct position to support the shoulder and the arm. This may reduce time and may be done without the help of another individual.

The shoulder section of the orthotic support is configured to be anchored to the wearer's torso, when worn. For example, the shoulder section may be anchored by straps which extend around a portion of the wearer's torso and hold the shoulder section in place on the shoulder. Preferably the shoulder support may be anchored to the wearer's torso by a torso section of the orthotic support, connected to the shoulders section, which may comprise an elastomeric base material and may be configured to conform to a portion of the wearer's torso.

In some embodiments the support may be a bespoke support designed to promote or facilitate supination or pronation of the arm for a specific individual. The position and strength of reinforcements may be specified for an individual wearer.

The resilient reinforcement of the orthotic support is configured to apply a rotational force to the wearer's arm, when worn, to urge a portion of the wearer's arm to rotate in a predetermined direction.

The resilient reinforcement is configured to apply a rotational force to the wearer's arm by positioning at least a portion of the reinforcement in a spiral around the sleeve section. The rotational force may be a torsional force. Preferably the resilient reinforcement is configured to apply a rotational force to a distal portion of the wearer's arm, for example to the wearer's hand and forearm.

The resilient reinforcement may exert a contractile force along its length when the orthotic support is donned by a wearer, as the presence of the wearer's body inside the support automatically stretches the resilient reinforcement in a certain direction. The reinforcement may then automatically apply a contractile force along its length in response to stretching.

By configuring at least a portion of the resilient reinforcement in a spiral around the sleeve section, the contractile force along the reinforcement is directed along the spiral so that it exerts a rotational force on the wearer's arm. The direction of the first torsional, or rotational, force may be determined by the direction in which the reinforcement is arranged in a spiral around the sleeve.

The reinforcement may extend in a spiral around at least a portion of the sleeve section. In other words, a portion of the reinforcement may be wound continuously around a portion of the sleeve section. The reinforcement may not necessarily extend in a spiral around the whole length of the sleeve section. As the reinforcement extends up the sleeve between the glove and the shoulder section, the reinforcement may be wound circumferentially around at least a portion of the sleeve in a spiral arrangement. For example, the reinforcement may extend helically around a portion of the sleeve section.

The sleeve section of the orthotic support may comprise an elbow section configured to encapsulate a wearer's elbow. The elbow section may be positioned, in use, around the wearer's elbow joint.

The reinforcement may preferably be configured to extend over the wearer's elbow joint, when worn. Particularly preferably, the reinforcement and the sleeve section may be configured to exert circumferential pressure on the wearer's elbow joint. In such an arrangement, the reinforcement may advantageously encourage extension of the wearer's elbow joint. This may advantageously counteract elbow flexion caused by a variety of medical conditions, for example cerebral palsy. Preferably the reinforcement may be configured to extend over a ventral portion (the inside) of the wearer's elbow joint, when worn.

In a preferred embodiment, the reinforcement extends in a spiral around a lower arm section of the sleeve section. The reinforcement may, for example, extend in a spiral around the sleeve section between the glove section and the elbow section. The reinforcement may extend over an upper arm section of the sleeve, for example from the elbow section to the shoulder section, in a non-spiral arrangement.

The reinforcement may be configured to extend in a spiral around the sleeve over a predetermined rotational angle. For example, the reinforcement may be configured to extend in a spiral around the sleeve around an angle of at least 270°, or at least 360°, or at least 450°, or at least 540°, along a longitudinal portion of the sleeve.

The length and pitch of the spiral may be controlled to control the rotational force exerted by the resilient reinforcement on the wearer's arm, in use. In other words, the angle of rotation over which the reinforcement is wound around the sleeve section, and the longitudinal length of the sleeve section over which the reinforcement is wound, may be varied to control the rotational force exerted by the reinforcement on the wearer's arm. The pitch of the spiral may vary along a longitudinal portion of the sleeve.

In a preferred embodiment of a right-handed orthotic support, a lower end of the reinforcement terminates at a thumb section of the glove section, and the reinforcement extends in a left-handed spiral around the sleeve until reaching the elbow section. Between the thumb section and the elbow section, the reinforcement winds fully around the sleeve section once, so that it has rotated through approximately 360 degrees. This arrangement of the reinforcement advantageously encourages supination of the wearer's right arm when worn.

The glove section preferably has a posterior side configured to be positioned, when worn, on the back of the wearer's hand, and an anterior side configured to be positioned, when worn, on the palm of the wearer's hand. The reinforcement preferably extends from the posterior side of the glove section, in a spiral around the sleeve, to the shoulder section.

One end of the reinforcement may be affixed, or attached, or anchored, to the glove section. By positioning an end of the reinforcement on glove section, the reinforcement may be configured such that the rotational force acts on the wearer's hand, to urge the wearer's hand, and the wearer's lower arm, to rotate in a predetermined direction.

The reinforcement preferably extends from a thumb portion of the glove section, around the sleeve, to the shoulder section.

The reinforcement, or a section of the reinforcement, may extend from the glove section, in a spiral around the sleeve, and over the shoulder section. Preferably the reinforcement, or a section of the reinforcement, may extend over the shoulder section to an edge of the orthotic support. Particularly preferably at least a portion of the reinforcement may extend over the shoulder section to an edge of a neck opening of the orthotic support, the edge of the neck opening being configured to sit adjacent to the wearer's neck when the support is worn.

Preferably an upper end of the reinforcement may be positioned on, or anchored to, the shoulder section. Preferably an upper end of the reinforcement may be positioned on a proximal edge of the shoulder section.

By positioning the reinforcement so that it extends to, or over, the shoulder section, the reinforcement may advantageously stabilise the wearer's arm. Unlike orthoses known in the art, the orthotic support of the present invention may thus support both the wearer's arm and shoulder together, providing greater stability to the shoulder and the wearer's elbow and wrist joints.

The reinforcement may be configured to apply a torsional force to the wearer's shoulder, radiating from the distal aspect of the wearer's forearm.

The reinforcement may advantageously apply a torsional force which urges the wearer's humeral head into the shoulder socket. The elastomeric base material of the sleeve section may advantageously provide a snug fit on the wearer's upper arm below the shoulder, and the positioning of the reinforcement panel over the shoulder section may counteract the effect of the arm's weight in pulling the humeral head downwards out of its socket.

In a preferred embodiment of the orthotic support, the reinforcement is configured to spiral around the sleeve section so that the rotational force urges supination of the wearer's forearm. Supination is the rotation of the wearer's arm outwards, away from the body.

A number of medical conditions, for example cerebral palsy, may result in pronation of a wearer's lower arm, so that the lower arm and hand are rotated inwards towards the body. The orthotic support may urge supination by providing a first rotational force which urges the wearer's arm to rotate outwards, away from the body. By configuring the reinforcement of the orthotic support to urge supination of the wearer's forearm, the orthotic support of the present invention may thus counteract the tendency of a wearer's arm to pronate towards the body. This may be particularly advantageous for a number of medical conditions.

The orthotic support may be configured to receive a wearer's right arm and right shoulder, in which case it may be termed a right-handed support, or it may be configured to receive a wearer's left arm and left shoulder, in which case it may be termed a left-handed support. Alternatively, the orthotic support may comprise two shoulder sections, two sleeve sections and two glove sections, and may be configured to receive both of the wearer's shoulders and arms.

If the orthotic device is a right-handed orthosis, in order to urge supination of the wearer's right arm the reinforcement may be configured to extend, or wind, around the sleeve section in a left-handed spiral.

A left-handed spiral is a spiral which, when looking down the central axis of the spiral, rotates anticlockwise moving away from the viewer. In other words, from the uppermost end of the spiral portion of the reinforcement, the reinforcement extends anticlockwise around the sleeve section as it extends towards the glove section.

This definition of spiral direction is consistent with standard terminology of right- or left-handed helices, for example as used when describing DNA.

A left-handed orthotic support may be a mirror-image of a right-handed support. Thus, if the orthotic device is a left-handed orthosis, in order to urge supination of the wearer's left arm the reinforcement may be configured to extend, or wind, around the sleeve section in a right-handed spiral.

A right-handed spiral is a spiral which, when looking down the central axis of the spiral, rotates clockwise moving away from the viewer. In other words, from the uppermost end of the spiral portion of the reinforcement, the reinforcement extends clockwise around the sleeve section as it extends towards the glove section.

In order to urge supination, the reinforcement may extend across a posterior side of the glove section, around the ulna, and diagonally across a ventral portion of the sleeve to an elbow section.

The reinforcement may, in other words, extend across a posterior side of the glove section, around the medial side of the wearer's wrist (with respect to the anatomical position), and diagonally across an anterior or ventral side of the wearer's forearm to an elbow section.

Alternatively, the reinforcement may extend across an anterior side of the glove section, around the radius, and diagonally across a posterior portion of the sleeve section to the elbow section. In this arrangement. the reinforcement may advantageously urge supination of the wearer's arm.

In another preferred embodiment of the present invention, the reinforcement is configured to spiral around the sleeve section so that the rotational force urges pronation of the wearer's forearm. Pronation is the rotation of the wearer's arm inwards, towards the body.

If the orthotic device is a right-handed orthosis, in order to urge pronation of the wearer's right arm the reinforcement may be configured to extend, or wind, around the sleeve section in a right-handed spiral.

If the orthotic device is a left-handed orthosis, in order to urge pronation of the wearer's left arm the reinforcement may be configured to extend, or wind, around the sleeve section in a left-handed spiral.

In order to urge pronation, the reinforcement may extend across a posterior side of the glove section, around the radius, and diagonally across a ventral portion of the sleeve section to an elbow section.

In an alternative embodiment, in order to urge pronation the reinforcement may extend across an anterior side of the glove section, around the ulna, and diagonally across a posterior portion of the sleeve section to an elbow section.

In a preferred embodiment, the resilient reinforcement may comprise a lower portion, or a lower arm portion, which is configured to extend in a spiral around a lower arm portion of the sleeve section. For example, the lower arm portion of the sleeve section may extend from the glove section to the elbow section.

The resilient reinforcement may comprise an upper portion, configured to extend from the elbow section of the sleeve section across a posterior side and/or an anterior side of the sleeve section to the shoulder section. The upper portion may be arranged in a non-spiral arrangement.

If the orthotic support is configured to encourage supination of the wearer's arm, the upper portion of the resilient reinforcement may preferably be arranged across a posterior, or dorsal, portion of the sleeve section, so that it is positioned, when worn, over the wearer's tricep. Such an arrangement may advantageously assist supination and prevent pronation by providing a force resisting movement of the upper arm towards the front of the wearer's body.

If the orthotic support is configured to encourage pronation of the wearer's arm, the upper portion of the resilient reinforcement may preferably be arranged across an anterior, or ventral, portion of the sleeve section, so that it is positioned, when worn, over the wearer's bicep. Such an arrangement may advantageously assist pronation and prevent supination by providing a force resisting movement of the upper arm away from the front of the user's body.

In a particularly preferred embodiment the upper portion of the resilient reinforcement comprises a plurality of branches extending over an upper arm section of the orthotic support to the shoulder section. A "branch" of the reinforcement may simply be a segment, or portion, or prong, of the reinforcement which is connected to the reinforcement at at least one end. Separate branches of the reinforcement may be connected to one another, and may extend in different directions on the orthotic support.

The use of a plurality of branches may advantageously provide greater stability to the wearer's shoulder and upper arm, in use. The use of a plurality of branches may advantageously allow each branch of the reinforcement to apply a force to the wearer's arm, when worn, to urge the wearer's arm in a predetermined direction. Each branch of the reinforcement may provide a force configured to act against movement of the wearer's upper arm away from that branch. By using several branches of the reinforcement, the wearer's upper arm and shoulder may be stabilised against movement in several directions.

Preferably the resilient reinforcement comprises a first branch configured to extend from above an elbow section over an anterior portion of the sleeve to the shoulder section, so that, when worn, the first branch is positioned over the wearer's bicep. The first branch may apply a force to the wearer's arm, when worn, to resist movement of the wearer's arm in a dorsal direction, away from the front of the user's body.

In addition to, or instead of, the first branch, the resilient reinforcement may comprise a second branch configured to extend from above the elbow section over a posterior portion of the sleeve to the shoulder section so that, when worn, the second branch is positioned over the wearer's tricep. The second branch may apply a force to the wearer's arm, when worn, to resist movement of the wearer's arm in a ventral direction, towards the front of the user's body.

The resilient reinforcement may comprise a third branch positioned between the first branch and the second branch. The third branch may be configured to extend from above the elbow section over a central portion of the sleeve to the shoulder section so that, when worn, the third branch is positioned over the wearer's deltoid. The third branch may apply a force to the wearer's arm, when worn, to resist movement of the wearer's arm in a lateral direction, outwardly away from the side of the user's body.

The use of one or more of the first, second and third branches of the reinforcement may advantageously stabilise the arm against movement in one or more direction. When the reinforcement comprises all of the first, second and third branches, the reinforcement may advantageously mimic the lineations of the wearer's shoulder muscles, and may thus act to support the user's muscles during use.

The upper portion of the reinforcement, which optionally includes one or more of the first, second and third branches, is preferably continuous with the lower portion of the reinforcement. By providing the upper and lower portions of the resilient reinforcement as a continuous resilient reinforcement, the reinforcement may advantageously transmit forces along the entire length of the wearer's arm from the shoulder section to the glove section.

The resilient reinforcement may exert a compressive force on the wearer's shoulder to reinforce the position of the humeral head in the glenoid fossa. For example, the reinforcement may compress the wearer's upper arm towards the wearer's body such that the humeral head of the shoulder is held more securely within the glenoid fossa.

The glove section may comprise a closable opening in a posterior portion of the glove section. Preferably the opening is closable using a fastening means such as a hook and loop fastener, or a zip.

The orthotic support may comprise more than one resilient reinforcement. In such a case the resilient reinforcement which extends from the glove section to the shoulder section may be termed the first resilient reinforcement.

Preferably the orthotic support additionally comprises a second resilient reinforcement configured to extend over a wrist portion of the orthotic support, and to apply a second force to the wearer's wrist, when worn, to urge extension or flexion of the wearer's wrist.

Preferably the second resilient reinforcement may be a reinforcement panel positioned on the posterior side of the glove section, and extending over a posterior section of the sleeve section so that it is positioned, in use, over a posterior side of the wearer's wrist. In this configuration, the second resilient reinforcement may urge extension of the wearer's wrist. This may advantageously counteract wrist flexion caused by medical conditions such as cerebral palsy.

Alternatively, the second resilient reinforcement may be positioned on the anterior side of the glove, and over an anterior side of the sleeve section so that it is positioned, in use, over the anterior side of the wearer's wrist. In this configuration, the second resilient reinforcement may urge flexion of the wearer's wrist.

In a preferred embodiment, the shoulder portion is configured to be anchored to the wearer's torso by a torso section which is configured to conform to at least a portion of the wearer's torso. Preferably the torso section comprises a third resilient reinforcement configured to generate a third force for facilitating scapula setting of the wearer's first scapula. Preferably the third resilient reinforcement, when worn, crosses the wearer's first scapula. Preferably the third resilient reinforcement, when worn, extends at least from the wearer's first clavicle.

Scapula setting may help to maintain the location of the wearer's humeral head within the glenoid fossa and thus help to prevent common shoulder instability injuries such as labral tears, dislocation or subluxation.

The orthotic support may comprise a fourth resilient reinforcement extending over the shoulder section from front to rear, so that, when worn, the fourth resilient reinforcement is positioned over the wearer's shoulder. The fourth resilient reinforcement may be configured to generate a fourth force to reduce subluxation of the wearer's shoulder.

According to a second aspect of the invention there may be provided a method of making an orthotic device according the first aspect of the invention, comprising the steps of: providing a shoulder section, a glove section and a sleeve section, the sleeve section connecting the shoulder section to the glove section, and each of the shoulder section, the glove section and the sleeve section comprising an elastomeric base material;
anchoring a first end of a resilient reinforcement to the glove section;
arranging a portion of the resilient reinforcement in a spiral around the sleeve section; and anchoring a second end of the resilient reinforcement to the shoulder section.

The resilient reinforcement is preferably attached to the elastomeric base material in a non-tensioned state. The reinforcement is preferably permanently attached to the elastomeric base material by stitching along its edges.

According to a third aspect of the present invention there is provided an orthotic support comprising:
a shoulder section for encapsulating a first shoulder of a wearer, configured to be anchored to the wearer's torso;
a sleeve section for conforming to at least a portion of the wearer's arm,
each of the shoulder section and the sleeve section comprising an elastomeric base material; and
a resilient reinforcement connected to the base material, the reinforcement comprising a first branch extending over an anterior portion of the sleeve section so that, when worn, the first branch is positioned over the wearer's bicep, and a second branch extending over a posterior portion of the sleeve section so that, when worn, the second branch is positioned over the wearer's tricep, so that the reinforcement is configured to apply a force to the wearer's upper arm, when worn, to urge the wearer's upper arm towards a predetermined rest position.

The first branch may apply a force to the wearer's arm, when worn, to resist movement of the wearer's arm in a dorsal direction, away from the front of the user's body.

The second branch may apply a force to the wearer's arm, when worn, to resist movement of the wearer's arm in a ventral direction, towards the front of the user's body.

The sleeve section may be a short sleeve, for example a sleeve configured to extend over and encapsulate the wearer's upper arm, in use. Alternatively, the sleeve section may be a long sleeve, for example a sleeve configured to extend over and encapsulate the wearer's upper arm, elbow joint, lower arm and wrist joint.

Preferably the first and second branches of the resilient reinforcement may extend over an upper portion of the sleeve section to a position proximal to, or above, the wearer's elbow joint, in use.

The resilient reinforcement may comprise a third branch positioned between the first branch and the second branch. The third branch may be configured to extend from above the elbow section over a central portion of the sleeve to the shoulder section so that, when worn, the third branch is positioned over the wearer's deltoid. The third branch may apply a force to the wearer's arm, when worn, to resist movement of the wearer's arm in a lateral direction, outwardly away from the side of the user's body.

The use of one or more of the first, second and third branches of the reinforcement may advantageously stabilise the arm against movement in one or more direction. When the reinforcement comprises all of the first, second and third branches, the reinforcement may advantageously mimic the lineations of the wearer's arm and shoulder muscles, and may thus act to support the user's muscles during use.

The upper portion of the reinforcement, which optionally includes one or more of the first, second and third branches, is preferably continuous with the lower portion of the reinforcement. By providing the upper and lower portions of the resilient reinforcement as a continuous resilient reinforcement, the reinforcement may advantageously transmit forces along the entire length of the wearer's arm from the shoulder section to the glove section.

The branches of the resilient reinforcement may exert a compressive force on the wearer's shoulder to reinforce the position of the humeral head in the glenoid fossa. For example, the reinforcement may compress the wearer's upper arm towards the wearer's body such that the humeral head of the shoulder is held more securely within the glenoid fossa. Multiple branches of reinforcement may better stabilise the humeral head by providing several compressive forces in different directions.

The orthotic support may additionally comprise a glove section for conforming to at least a portion of the wearer's hand, the glove section comprising an elastomeric base material.

The sleeve section may thus comprise a long sleeve configured to connect the glove section to the shoulder section.

The branches of the resilient reinforcement preferably converge at a point proximal to, or above, an elbow section of the orthotic device. Having multiple branches of the reinforcement converging provides a single reinforcement panel with multiple branches, or prongs, extending over the sleeve section in different directions. This may advantageously allow forces to be transmitted through the branches of the reinforcement, to better stabilise the wearer's upper arm and shoulder.

Where the orthotic support is short-sleeved, the branches of the resilient reinforcement preferably converge at a point proximal to the lower end of the sleeve.

When the support is long-sleeved and comprises a glove section, the branches of the reinforcement preferably converge into a reinforcement panel which extends to the glove section. Particularly preferably, the reinforcement panel extends in a spiral around the sleeve section to the glove section.

Further features of the orthotic support may be as described above in relation to the first aspect of the invention.

There may be provided a use of an orthotic support, as described in any form above, for the treatment or prevention of arm over-pronation, arm over-subluxation, elbow flexion or extension, and/or wrist flexion or extension.

There may be provided a use of an orthotic support, as described in any form above, for the treatment or prevention of shoulder instability injuries. Shoulder instability injuries may include dislocation, subluxation and labral tears.

The orthotic support may also be used as an injury management tool alongside physiotherapy.

BRIEF DESCRIPTION OF THE DRAWINGS

An embodiment of the invention will now be described, by way of example, and with reference to the accompanying drawings, in which.

DETAILED DESCRIPTION OF EXAMPLE EMBODIMENT

Figure 1:
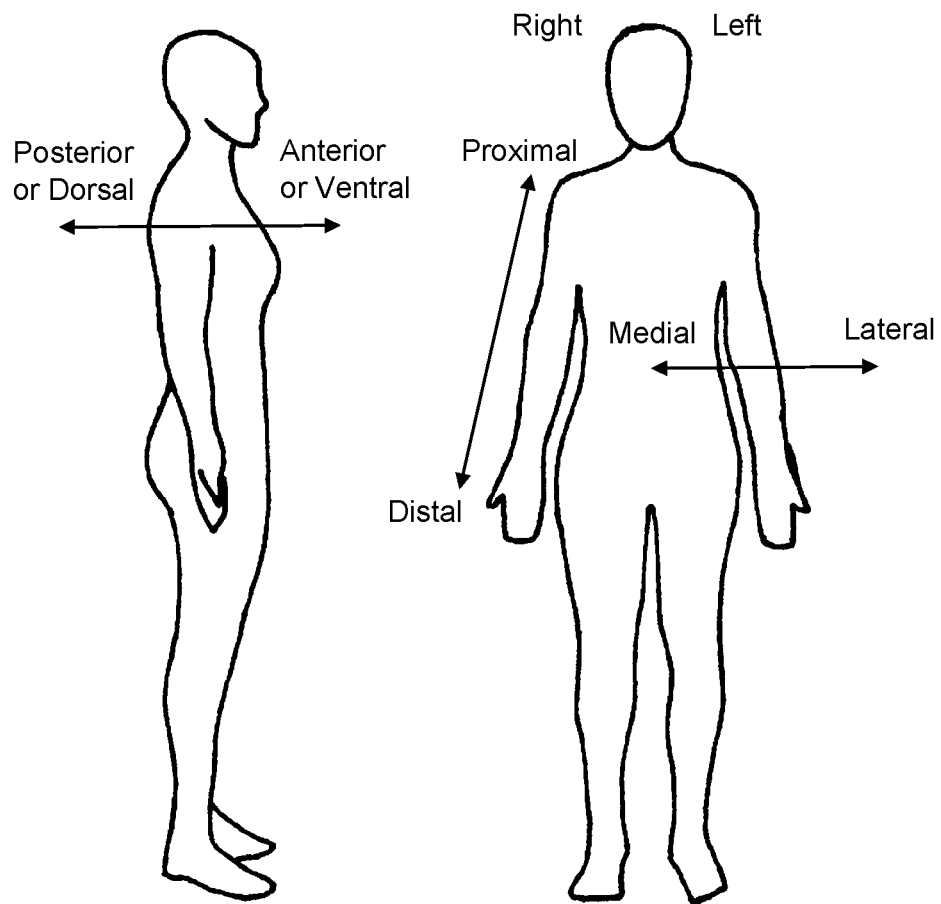
FIG. 1 shows a schematic diagram illustrating a human body in the standard anatomical position.
Figure 2:
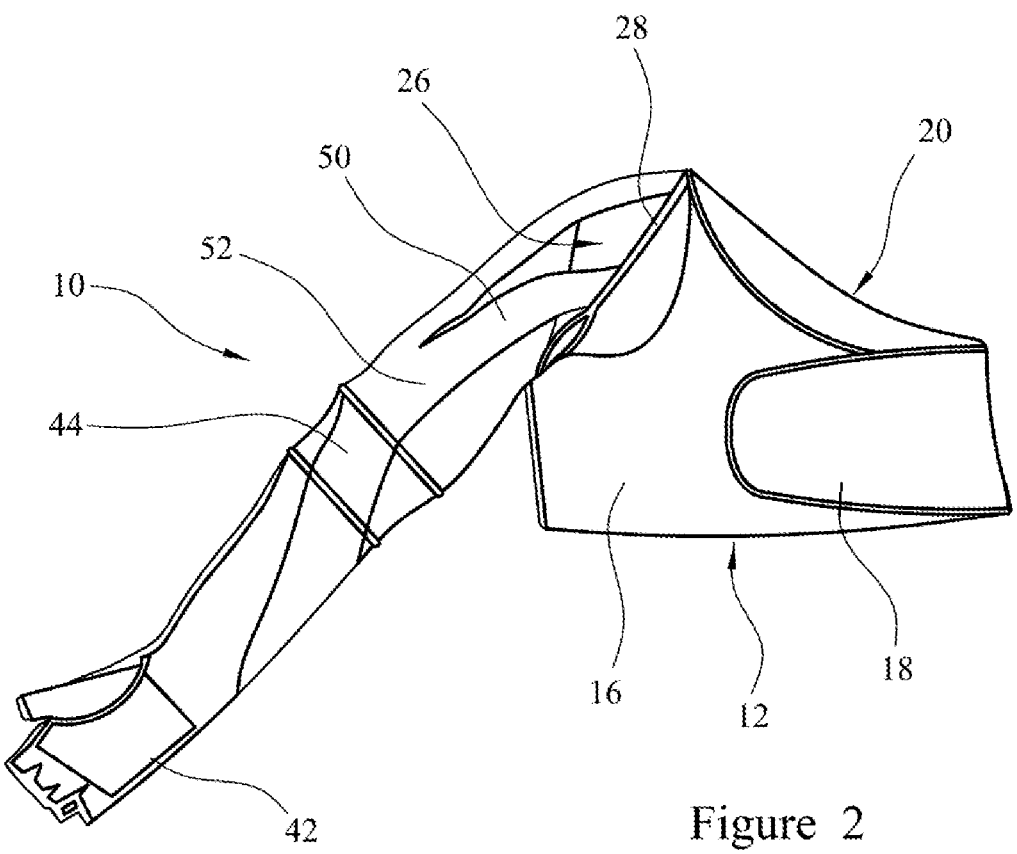
FIG. 2 shows a front view of a right-handed orthotic support according to a preferred embodiment of the preferred invention.
Figure 3:
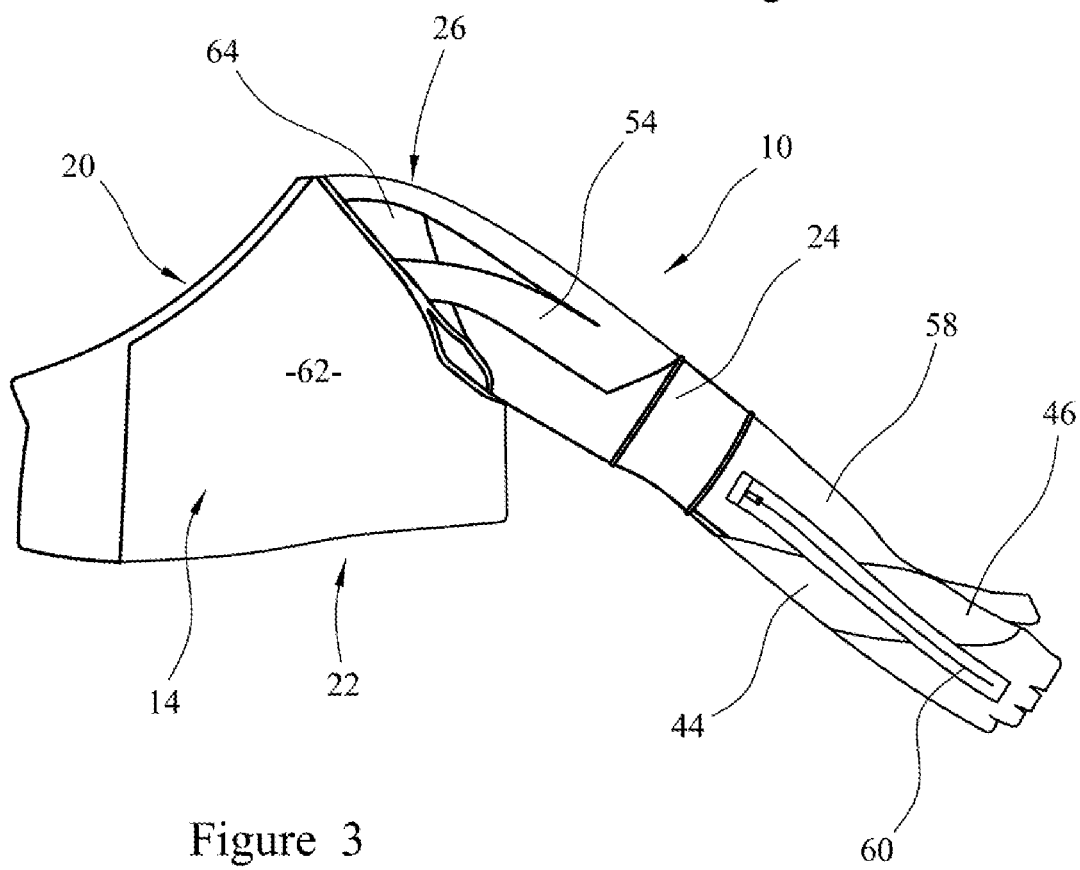
FIG. 3 shows a rear view of a right-handed orthotic support according to a preferred embodiment of the preferred invention.
Figure 4:
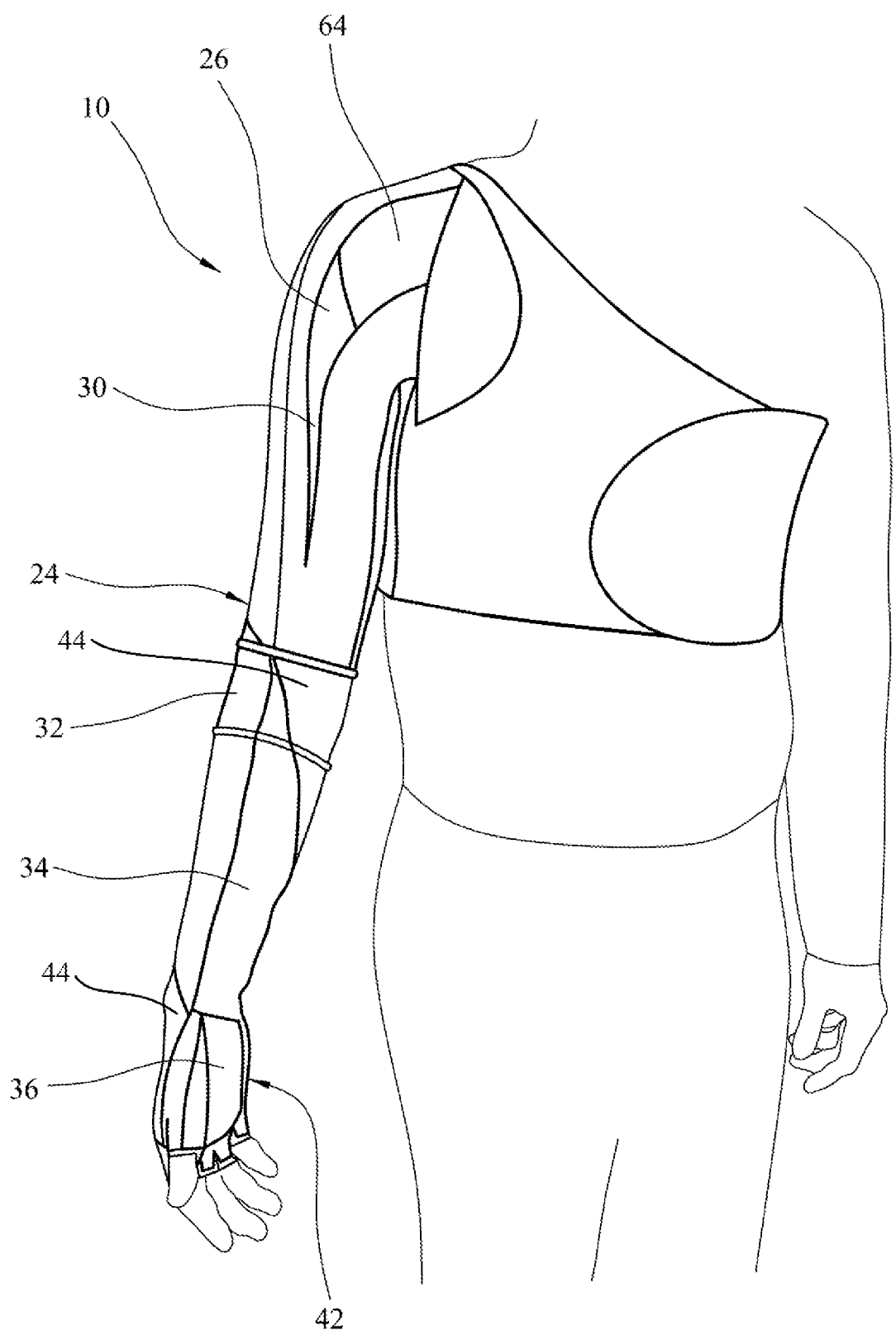
FIG. 4 shows a front view of the orthotic support of FIG. 4, when worn by a wearer.
Figure 5:
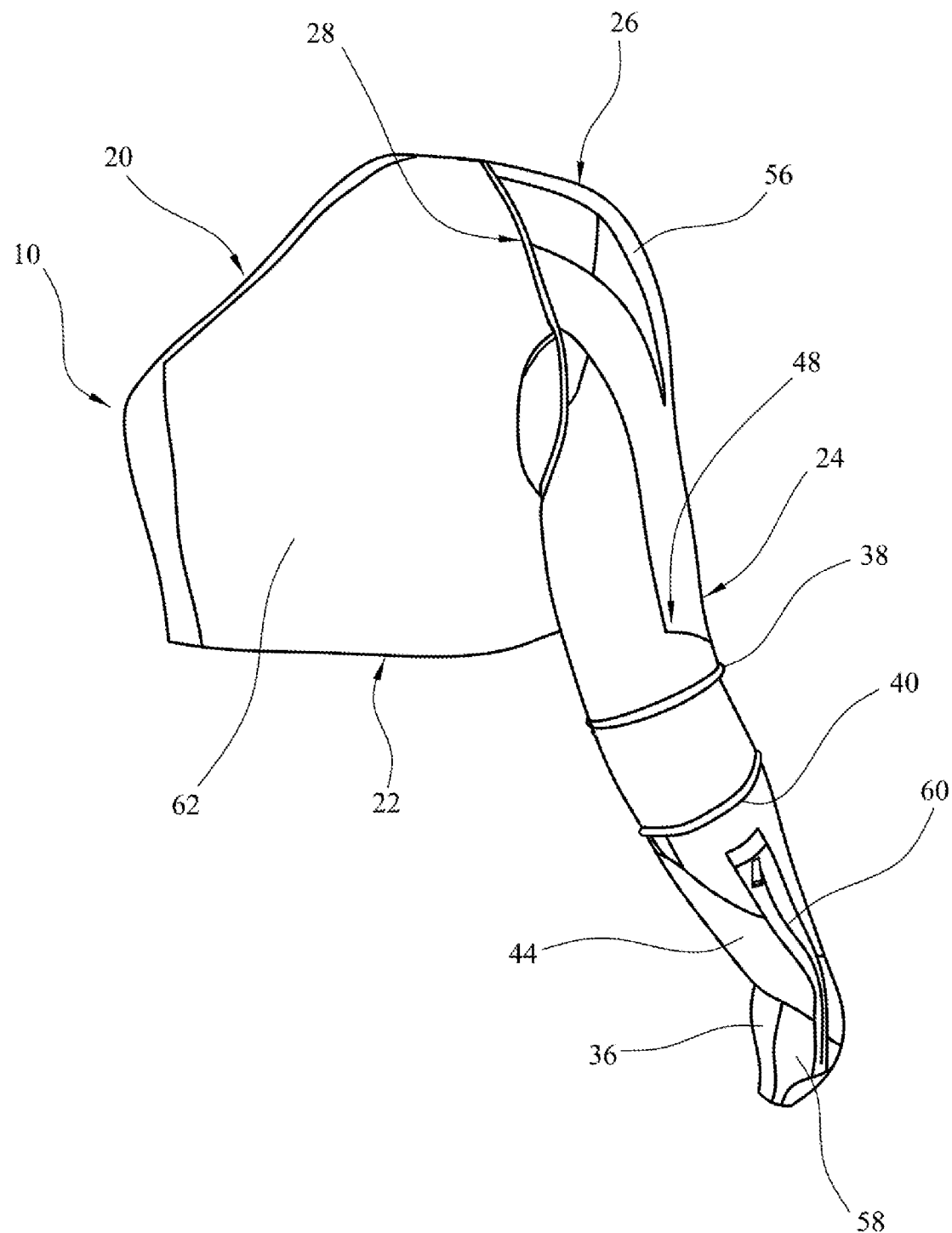
FIG. 5 shows a rear perspective view of the orthotic support of FIG. 4.
Figure 6:
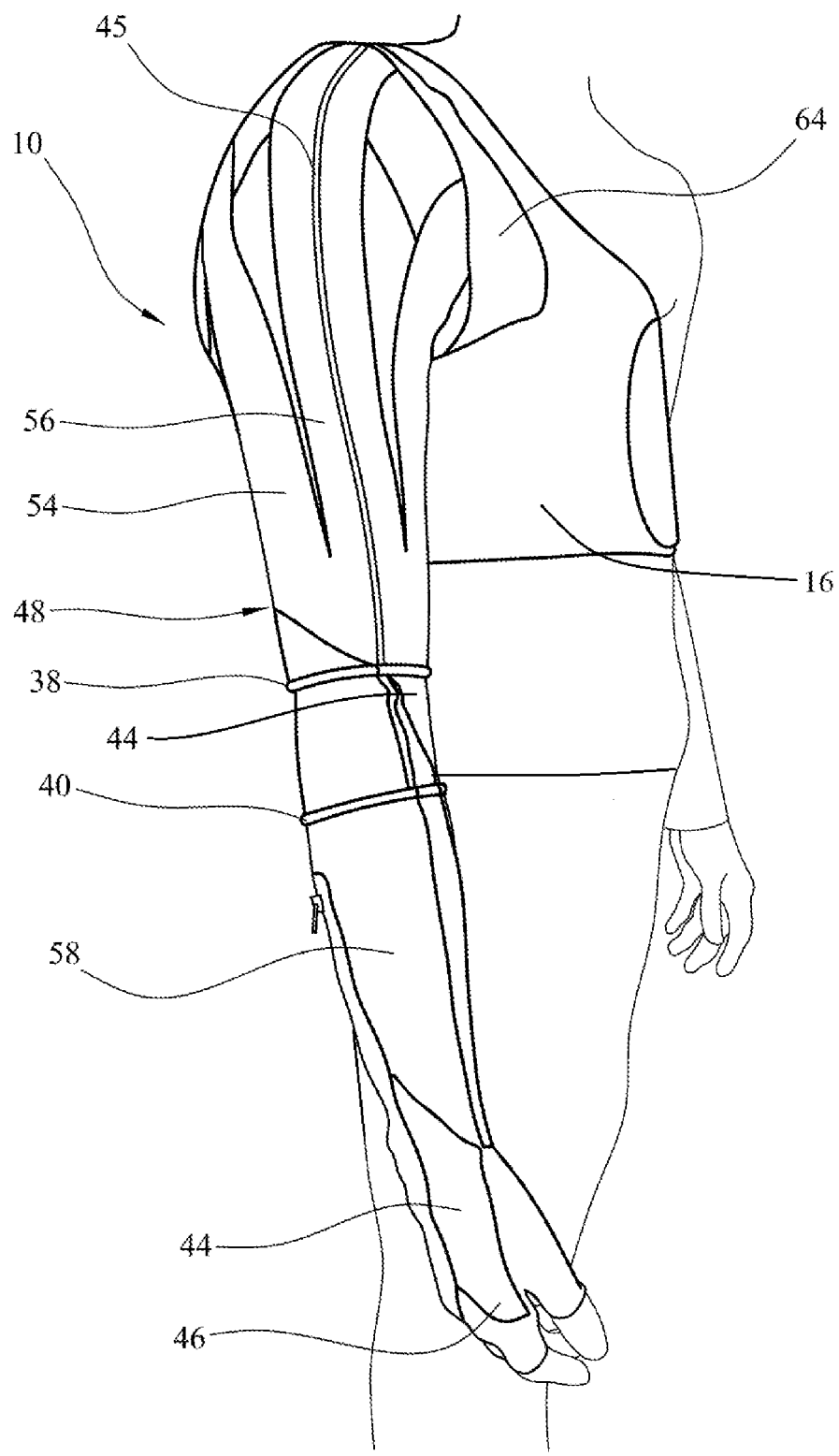
FIG. 6 shows a right side view of the orthotic support of FIG. 4, when worn by a wearer.
Figure 7:
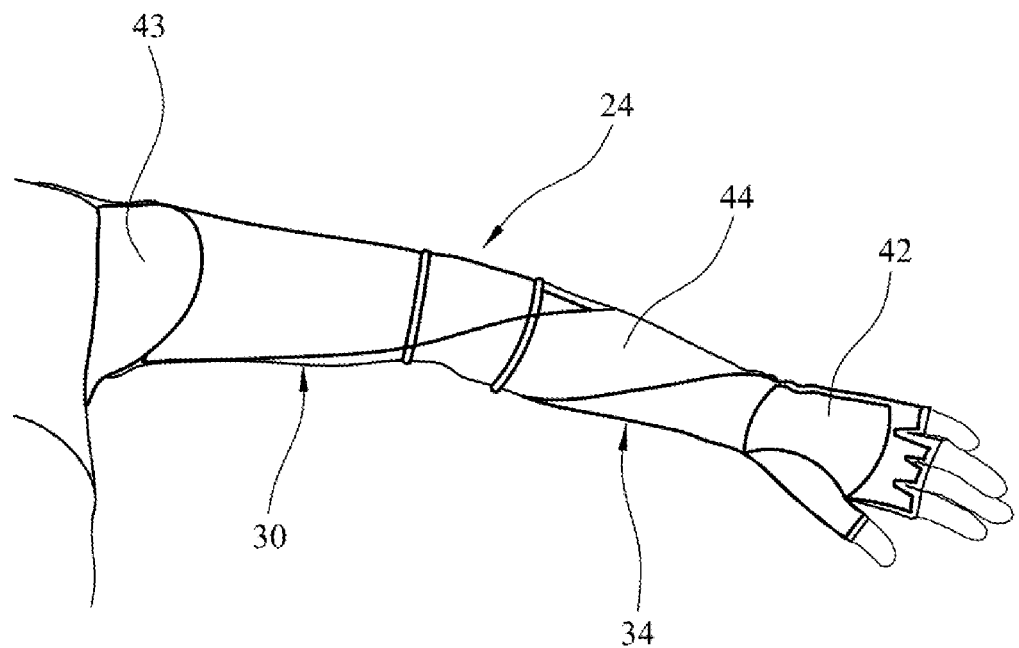
FIG. 7 shows a rear underside view of the sleeve section orthotic support of FIG. 4, when worn by a wearer.

FIG. 1 illustrates a human body in the standard anatomical position. Terminology used throughout this document will be made with reference to a body in the anatomical position.

As shown in FIG. 1, the "anatomical position" defines a position in which a person is standing with the thumb of each hand turned outwards, so that the palms of the person's hands face forwards. The direction outwards from the front (belly side) of the body in this position may be termed "anterior" or "ventral", while the direction outwards from the back of the body may be termed "posterior" or "dorsal". The direction laterally inwards towards the middle of the body in this position may be termed "medial", while the direction laterally outwards away from the sides of the torso may be termed "lateral". The direction towards the end of a limb which joins the body may be termed "proximal", while the direction towards the end of the limb furthest from the joint with the body may be termed "distal".

A right-handed orthotic support 10 according to a first preferred embodiment of the invention is shown in FIGS. 1 to 7.

The orthotic support 10 is a combined hand, wrist, elbow and shoulder orthosis, which is configured to be worn on a wearer's right arm and right shoulder. It has a torso section, or upper-body section, 12 manufactured predominantly from a resilient elastomeric material having a composition of 51% polyamide, 17% cotton and 32% DORLASTAN. This material is a lightweight, breathable, elastomeric fabric and is suitable for forming the underlying material of the support 1. Other suitable fabrics are available, for example under the trade names SPANDEX or LYCRA.

The torso section 12 has a posterior panel 14 configured to sit against the wearer's back, when worn, and right and left front flaps 16, 18 which are fastenable to one another over the front of the wearer's body with a hook-and-loop fastening. The rear panel 14 and the left front flap 18 have a sloping upper edge so that the left front flap can pass under the wearer's left arm pit, when worn. When the front flaps 16, 18 are fastened to one another, the torso section defines a neck-and-left-arm opening 20 through which the wearer's neck and left arm extend, in use, and a torso opening 22 through which the wearer's torso extends when worn.

A right sleeve 24 is attached to the torso section 12 to form a right shoulder section 26. A right shoulder ring seam 28 runs from the top of the neck-and-left-arm opening 20 over a front part of the right shoulder section 26 down to the right sleeve 24, around the underside of the right sleeve, over a back part of the right shoulder section and back up to the top of the neck-and-left-arm opening.

A right under-arm seam runs underneath the right sleeve 24 between two points on the right shoulder ring seam 28. Defined between the right shoulder ring seam and the right under-arm seam is a right armpit portion 43 manufactured from soft cotton.

The right sleeve 24 is a long sleeve with an upper sleeve section 30, an elbow section 32, and a lower sleeve section 34 which terminates in a glove section 36.

A right sleeve seam 45 runs along the top side of the right sleeve 24 between the glove section 36 and the right shoulder ring seam 28.

The upper section 30 of the sleeve extends from the shoulder section down to a position just above (just proximal) to the wearer's elbow joint, in use, and is connected to the elbow section by a stitched upper elbow ring seam 38 which extends circumferentially around the sleeve.

The elbow section 32 is configured to be positioned around a wearer's elbow joint, in use. The elbow section 32 is connected to the lower section 34 of the sleeve by a lower elbow ring seam 40. The elbow section and the upper and lower elbow ring seams may advantageously provide freedom of movement of the wearer's elbow joint, while maintaining compression from the sleeve above and below the elbow joint.

The lower sleeve section 34 is connected to a glove section 36 which is partially formed from the same panel of elastomeric base material as the lower sleeve section 34.

The glove section 36 is finger-less, and has a thumb opening and four finger openings through which the wearer's fingers and thumb may extend, in use. The anterior, palm, side 42 of the glove section is partially covered in a rubberised mesh material to improve the wearer's grip.

The sleeve 24 and the glove section 36 are formed from the same elastomeric base material as the torso section 12.

A first reinforcement panel 44 is fabricated from a resilient material having a composition of 81% polyamide and 19% Lycra®, which is an elastomeric material that offers greater resistance to deformation than the underlying elastomeric base material forming the torso section 12. This reinforcement panel 44 is joined to the torso section 12 by a first panel seam (not shown) extending around the edge of the first reinforcement panel.

The first reinforcement panel 44 has a first end 46 which is positioned on a posterior side of the glove section 36, adjacent to the thumb of the glove section. The first reinforcement panel extends from the first end 46 in an anti-clockwise spiral around the lower sleeve section 34 (anti-clockwise if looking down the sleeve away from the elbow section). The first reinforcement panel extends diagonally across the posterior side of the glove section 36, around the ulna (the medial side of the wrist), and diagonally across the anterior, or ventral, side of the lower sleeve section 34 to the elbow section 32. The first reinforcement panel extends across the anterior side of the elbow section 32 between the lower elbow ring seam 40 and the upper elbow ring seam 38, and across the upper elbow ring seam 38 onto the upper section 30 of the sleeve.

On the upper section 30 of the sleeve, the first reinforcement panel 44 diverges into three branches, or prongs, each of which extends over a different part of the upper section 30 to the right shoulder ring seam 28.

A first branch 50 of the first reinforcement panel 44 diverges from the panel at a bicep position 52 on an anterior side of the upper section 30 of the sleeve. The bicep position 52 is located approximately midway across the anterior side of the sleeve, at a point that will be located, when the orthosis is worn, over the distal end of the wearer's bicep. From the bicep position, the first branch 50 of the panel 44 extends linearly up the upper section 30, in an arrangement that aligns with the direction of the wearer's bicep when the orthosis is worn. When the first branch 50 reaches the shoulder section 26 at the proximal end of the sleeve 24, the first branch curves towards, and connects to an anterior portion of the right shoulder ring seam 28.

Above the upper elbow ring seam 38, the first reinforcement panel 44 continues along its spiral trajectory around the sleeve until it reaches a tricep position 48 on the posterior side of the upper section 30. The tricep position 48 is located approximately midway across the posterior side of the sleeve, at a point that will be located, when the orthosis is worn, over the distal end of the wearer's tricep.

At the tricep position, the first reinforcement panel 44 ceases to spiral around the sleeve. A second branch 54 of the reinforcement panel 44 extends from the tricep position over an anterior portion of the sleeve. The second branch 54 extends linearly up the upper section 30 of the sleeve, in an arrangement that aligns with the direction of the wearer's tricep when the orthosis is worn. When the second branch 54 reaches the shoulder section 26 at the proximal end of the sleeve 24, the second branch curves towards, and connects to a posterior portion of the right shoulder ring seam 28.

A third branch 56 of the first reinforcement panel 44 is positioned in between the first and second branches 50, 54. The third branch 56 extends linearly up the upper section 30 of the sleeve, in alignment with the right sleeve seam 45, and over the shoulder section 26 so that the third branch extends over a central portion of the wearer's deltoid, when worn. The third branch 56 connects to, and terminates at, a top portion of the right shoulder ring seam 28, at an edge of the neck-and-left-arm opening 20.

A second resilient reinforcement panel 58, formed from the same material as the first reinforcement panel 44, is attached to the posterior side of the glove section 36 and lower section of the sleeve. The second resilient reinforcement panel 58 extends from the finger and thumb openings to the lower elbow ring seam 40. The second resilient reinforcement panel 58 is attached to the elastomeric base material of the glove section and lower section of the sleeve, and is positioned underneath the first resilient reinforcement panel 44.

A wrist opening 60, closable with a zip, is located on the posterior side of the glove section 36 and lower section of the sleeve. Both the first and second reinforcement panels 44, 58 are stitched to the elastomeric base material along the edges of the wrist opening 60. When the zip is open, the wrist opening 60 extends through both reinforcement panels, and through the elastomeric base material, into the interior of the sleeve 26. When the zip is closed, however, the stitching around the edges of the opening 60 means that forces can be transmitted across the zip along the longitudinal axes of the reinforcement panels 44, 58.

A third resilient reinforcement panel 62, formed from the same resilient material as the first and second panels 44, 58, is attached to the posterior panel 14 of the torso section 12. The third reinforcement panel 62 extends from the torso opening to the neck-and-left-arm opening 20 so that it is positioned, when worn, over the right scapula of the wearer.

A fourth resilient reinforcement panel 64, formed from the same resilient material as the first and second panels 44, 58, is arranged to extend over the shoulder section 24. The fourth resilient reinforcement panel 64 extends from the posterior side of the right shoulder ring seam 28, over the shoulder section 24 and over the anterior side of the right shoulder ring seam 28 onto the right front flap 16. The fourth reinforcement panel 64, when worn, extends over the wearer's right clavicle.

In use, a wearer may don the orthotic support 10 by opening the hook and loop fastening to separate the right and left front flaps 16, 18, and inserting their right arm into the sleeve 24. The wrist opening 60 may be opened by opening the zip, in order to facilitate donning of the sleeve and glove section, after which the wrist opening should be closed. When correctly worn, the wearer's hand is received in the glove section, the elbow section is positioned around the wearer's elbow joint, and the wearer's shoulder is encapsulated in the shoulder section of the support. The provision of the sleeve and glove section in a one-piece orthosis with the shoulder section and torso section advantageously means that the sleeve and glove section are always correctly aligned on the wearer's arm when the support is worn.

The torso section 12 is fastened by passing the left front flap 18 under the wearer's left arm pit, and fastening the left and right front flaps together using the hook and loop fastener.

The elastomeric base material of the torso section, shoulder section, sleeve and glove section is automatically stretched when the wearer dons the support 10, so the elastomeric base material exerts a compressive force on the wearer's body. This may advantageously improve the wearer's proprioception.

Donning the orthotic support 10 also causes the resilient material of the first, second, third and fourth resilient reinforcement panels to be automatically stretched, such that the resilient reinforcement panels automatically exert a contractile force which urges the wearer's body in a predetermined direction. The resilient reinforcement panels may advantageously generate forces to urge against movement of the wearer's body in a direction that causes the reinforcement panels to stretch.

While the actual forces on the wearer's body will be an additive result of the forces exerted by different resilient panels, the effect of each reinforcement panel may be considered separately.

When the orthotic support 10 is worn, the first reinforcement panel 44 exerts a rotational force on the wearer's arm. As the first reinforcement panel 44 is arranged in a left-handed (anticlockwise) spiral around the lower section of the sleeve, the first panel 44 exerts a contractile force when stretched, which urges the wearer's lower arm to rotate clockwise (looking from the shoulder towards the hand). Thus, the first reinforcement panel 44 exerts a rotational force on the wearer's hand and lower arm which urges supination of the wearer's arm. This may advantageously counteract pronation of the arm which may result from a number of medical conditions.

The first reinforcement panel 44 also urges extension of the wearer's elbow joint, as flexion of the elbow stretches the first reinforcement panel 44.

The first reinforcement panel 44 advantageously transmits contractile forces along its length between the shoulder section and the glove section, which may increase the magnitude of the rotational force that is generated on the wearer's arm in use.

The three-branch configuration of the first reinforcement panel 44 on the upper section of the sleeve may advantageously spread the applied forces over a wide area of the wearer's upper arm to improve arm stability. The three-branch configuration may also provide improved stability to the wearer's shoulder joint, as all three branches may exert a compressive force encouraging correct location of the shoulder joint, and movement of the shoulder in any direction may generate a corrective force from one or more of the first, second and third branches.

The second reinforcement panel 58 advantageously urges extension of the wearer's wrist joint, as its position on the posterior side of the sleeve and glove section means that it is stretched by flexion of the wrist. The second panel 58 may thus counteract natural wrist flexion caused by a variety of medical conditions.

The third reinforcement panel 62 may advantageously provide a compressive force on the wearer's right scapula, to urge scapula setting. As the third panel would have stretched when the support was donned, the panel 62 exerts a contractile force in a direction extending from the wearer's shoulder diagonally downwards across the wearer's back.

This has the effect of urging the wearer's shoulder back and slightly downwards. This, in turn, urges the wearer's right scapula to retract towards the wearer's spine. The humeral head is thus placed in a more favourable position with respect to the glenoid fossa.

The fourth resilient reinforcement panel 64 may advantageously be configured to generate a force to reduce subluxation of the wearer's shoulder.

The orthotic support 10 may thus exert a number of corrective forces on the wearer's body, to urge the wearer's arm and shoulder into a desirable postural position. The orthotic support may thus be useful in correcting existing muscular conditions, improving instability of certain body parts, or in rehabilitation of injuries.

While the features of the present invention have been described mainly in relation to a right-handed orthotic support configured to encourage supination of a wearer's arm, the orthotic support of the present invention may be adapted to instead encourage pronation by reversing the direction in which the first reinforcement panel spirals around the sleeve.

Figure 8:
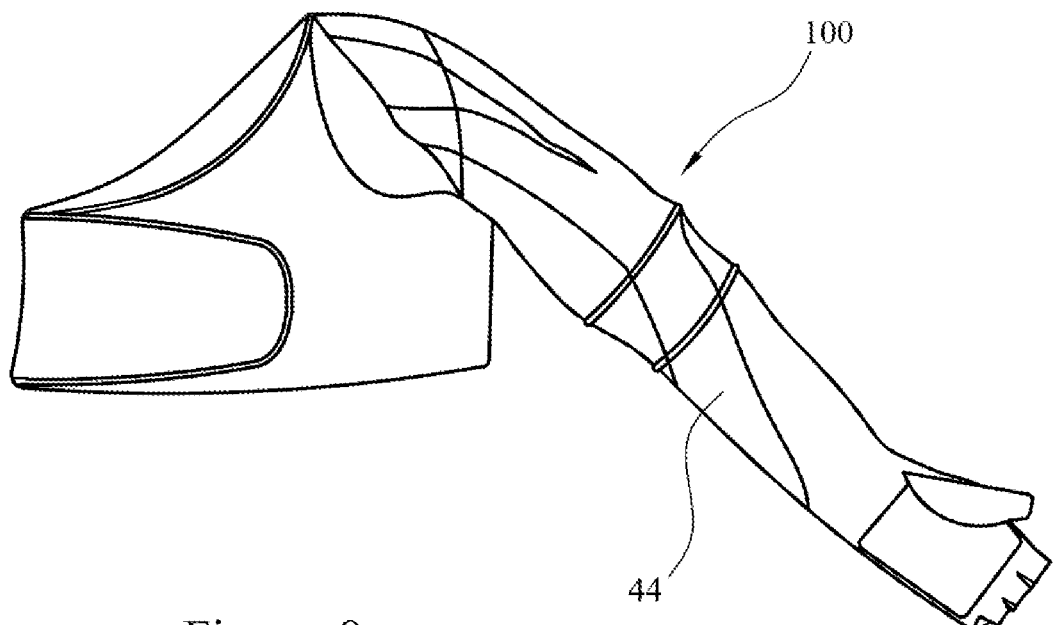
FIG. 8 shows a front view of a left-handed orthotic support according to a preferred embodiment of the preferred invention.

A left-handed orthotic support 100 according to a second preferred embodiment of the invention is shown in FIG. 8. The left-handed orthotic support 100 is effectively a mirror-image of the right-handed orthotic support 10.

Figure 9:
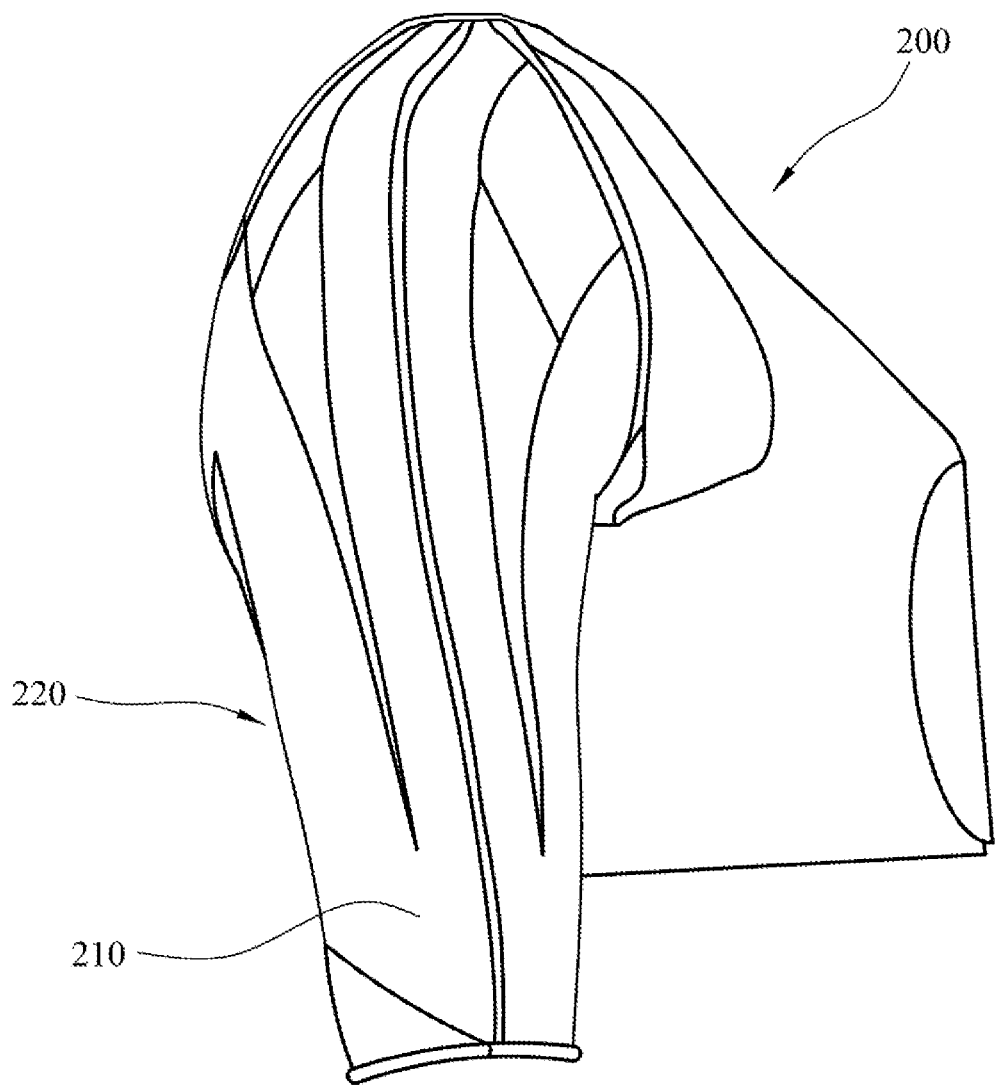
FIG. 9 shows a right side view of a short-sleeved right-handed orthotic support according to a preferred embodiment of the present invention.

FIG. 9 shows another preferred embodiment of an orthotic support 200 according to a preferred embodiment of the present invention. The support 200 of FIG. 9 is a short-sleeved orthosis, which is substantially identical to the torso section, shoulder section, and upper sleeve section of the orthotic support 10 in FIGS. 1 to 7.

The sleeve 220 of the support 200 extends only as far as the upper elbow ring seam of the orthotic support 10, and does not have a connected lower sleeve section or glove section. In an alternative embodiment, the support 200 could have a long sleeve and optionally a glove section.

The orthotic support 200 has the same three-branch configuration of the first resilient reinforcement panel 210. As described above, this arrangement may advantageously spread stabilising forces over a wide area of the wearer's upper arm to improve arm stability. The three-branch configuration may also provide improved stability to the wearer's shoulder joint, as all three branches may exert a compressive force encouraging correct location of the shoulder joint. Movement of the shoulder in any direction may generate a corrective force from one or more of the first, second and third branches, so that the upper arm and shoulder are always urged back into a desired rest position. The alignment of the first, second and third branches of the reinforcement panel over the wearer's major shoulder and upper arm muscles may advantageously provide a strengthening and stabilising effect on the wearer, as the resiliency of the branches may naturally mimic and assist the wearer's muscles during movement.

The orthotic support 200 may thus provide improved scapula setting, reduction of shoulder subluxation, and improved stability of the upper arm.

The invention claimed is:

1. An orthotic support, comprising:
a shoulder section for encapsulating a shoulder of a wearer, wherein the shoulder section is configured to be anchored to the wearer's torso;
a glove section for conforming to at least a portion of the wearer's hand;
a sleeve section for conforming to the wearer's arm, wherein the sleeve section connects the shoulder section to the glove section, wherein the shoulder section, the glove section, and the sleeve section comprising include an elastomeric base material that extends from the glove section to the shoulder section, and wherein the sleeve section includes an upper section, a lower section, and an elbow section between the upper section and the lower section; and
a resilient reinforcement that is connected to the elastomeric base material, wherein the resilient reinforcement includes at least a spiral portion of the resilient reinforcement extends in a spiral around the sleeve section so that the resilient reinforcement is configured to apply a rotational force to the wearer's arm, when worn, to urge a portion of the wearer's arm to rotate in a predetermined direction, wherein the resilient reinforcement further includes a plurality of branches configured to extend over the upper section of the sleeve section to the shoulder section,
wherein the plurality of branches includes:
a first branch configured to extend from above the elbow section of the sleeve section over an anterior portion of the sleeve section to the shoulder section so that the first branch is configured to be positioned over the wearer's bicep when worn;
a second branch configured to extend from above the elbow section of the sleeve section over a posterior portion of the sleeve section to the shoulder section so that the second branch is configured to be positioned over the wearer's tricep when worn; and
a third branch positioned between the first branch and the second branch, wherein the third branch is configured to extend from above the elbow section of the sleeve section over a central portion of the sleeve section to the shoulder section so that the third branch is configured to be positioned over the wearer's deltoid when worn.

2. An orthotic support according to claim 1, wherein the spiral portion of the resilient reinforcement is configured to spiral around the lower section of the sleeve section so that the rotational force urges supination of the wearer's forearm.

3. An orthotic support according to claim 2, wherein the orthotic support is configured to receive the wearer's right arm, and wherein the spiral portion of the resilient reinforcement is configured to extend around the lower section of the sleeve section in a left-handed spiral in order to urge supination of the wearer's right arm.

4. An orthotic support according to claim 2, wherein the orthotic support is configured to receive the wearer's left arm, and wherein the spiral portion of the reinforcement is configured to extend around the lower section of the sleeve section in a right-handed spiral in order to urge supination of the wearer's left arm.

5. An orthotic support according to claim 2, wherein the resilient reinforcement is configured to extend across a posterior side of the glove section, around the wearer's ulna, and diagonally across a ventral portion of the sleeve section to the elbow section of the sleeve section for encapsulating the wearer's elbow.

6. An orthotic support according to claim 2, wherein the resilient reinforcement is configured to extend across an anterior side of the glove section, around the wearer's radius, and diagonally across a posterior portion of the sleeve section to the elbow section of the sleeve section.

7. An orthotic support according to claim 2, wherein the upper section of the sleeve section of the resilient reinforcement extends from the elbow section of the sleeve section across a posterior side and/or an anterior side of the sleeve section to the shoulder section.

8. An orthotic support according to claim 1, wherein in which the spiral portion of the resilient reinforcement is configured to spiral around the lower section of the sleeve section so that the rotational force urges pronation of the wearer's forearm.

9. An orthotic support according to claim 8, wherein the orthotic support is configured to receive the wearer's left arm, and wherein the spiral portion of the resilient reinforcement is configured to extend around the lower section of the sleeve section in a left-handed spiral in order to urge pronation of the wearer's left arm.

10. An orthotic support according to claim 8, wherein the resilient reinforcement is configured to extend extends across a posterior side of the glove section, around the wearer's radius, and diagonally across a ventral portion of the sleeve section to the elbow section of the sleeve section.

11. An orthotic support according to claim 7, wherein the resilient reinforcement is configured to extend across an anterior side of the glove section, around the wearer's ulna, and diagonally across a posterior portion of the sleeve section to the elbow section of the sleeve section.

12. An orthotic support according to claim 8, wherein the orthotic support is configured to receive the wearer's right arm, and wherein the spiral portion of the resilient reinforcement is configured to extend around the lower section of the sleeve section in a right-handed spiral in order to urge pronation of the wearer's right arm.

13. An orthotic support according to claim 1, further comprising a second resilient reinforcement configured to extend over a wrist portion of the orthotic support, and to apply a second force to the wearer's wrist, when worn, to urge extension or flexion of the wearer's wrist.

14. An orthotic support according to claim 1, wherein the shoulder portion is configured to be anchored to the wearer's torso by a torso section configured to conform to at least a portion of the wearer's torso.

15. An orthotic support according to claim 14, wherein the torso section comprises a third resilient reinforcement configured to generate a third force for facilitating scapula setting of the wearer's first scapula.

16. An orthotic support according to claim 1, further comprising a fourth resilient reinforcement extending over the shoulder section from front to rear, in which the fourth resilient reinforcement is configured to generate a fourth force to reduce subluxation of the wearer's shoulder.

17. The use of an orthotic support according to claim 1 for the treatment or prevention of shoulder dislocation or shoulder subluxation.

18. The use of an orthotic support according to claim 1 for the treatment or prevention of arm over-pronation or over-supination, wrist flexion or elbow flexion.

19. An orthotic support, comprising:
a shoulder section for encapsulating a first shoulder of a wearer, wherein the shoulder section is configured to be anchored to the wearer's torso;
a sleeve section for conforming to at least a portion of the wearer's arm, wherein the sleeve section is connected to the shoulder section, wherein the shoulder section and the sleeve section include an elastomeric base material; and
one or more resilient reinforcements connected to the elastomeric base material, wherein the one or more reinforcements includes a first branch extending over an anterior portion of the sleeve section and configured to be positioned over the wearer's bicep when worn, a second branch extending over a posterior portion of the sleeve section and configured to be positioned over the wearer's tricep when worn, and a third branch positioned between the first branch and the second branch, wherein the third branch extends over a central portion of the sleeve section to the shoulder section and is configured to be positioned over the wearer's deltoid when worn, so that the first, second, and third branches of the one or more resilient reinforcements are configured to apply a force to the wearer's upper arm, when worn, to urge the wearer's upper arm towards a predetermined rest position.

20. An orthotic support according to claim 19, further comprising a glove section for conforming to at least a portion of the wearer's hand, wherein the glove includes an elastomeric base material, wherein the sleeve section connects the glove section to the shoulder section.

21. An orthotic support according to claim 20, wherein the first, second, and third branches of the one or more resilient reinforcements converge above an elbow section of the orthotic device into a resilient reinforcement panel which extends to the glove section.

22. An orthotic support according to claim 21, wherein the sleeve section further includes an elbow section, wherein the resilient reinforcement panel extends from the elbow section, in a spiral around the sleeve section, to the glove section, so that the reinforcement panel is configured to apply a rotational force to the wearer's arm, when worn, to urge a portion of the wearer's arm to rotate in a predetermined direction.

* * * * *